US010661102B2

(12) United States Patent
Clayton et al.

(10) Patent No.: US 10,661,102 B2
(45) Date of Patent: May 26, 2020

(54) TREATMENT ENERGY DELIVERY SYSTEM

(71) Applicant: Varian Medical Systems, Inc., Palo Alto, CA (US)

(72) Inventors: James E. Clayton, Saratoga, CA (US); Mark E. Trail, Menlo Park, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 153 days.

(21) Appl. No.: 15/476,550

(22) Filed: Mar. 31, 2017

(65) Prior Publication Data
US 2018/0280734 A1 Oct. 4, 2018

(51) Int. Cl.
*A61N 5/10* (2006.01)

(52) U.S. Cl.
CPC .......... *A61N 5/1083* (2013.01); *A61N 5/1082* (2013.01); *A61N 2005/1022* (2013.01); *A61N 2005/1087* (2013.01); *A61N 2005/1089* (2013.01); *A61N 2005/1094* (2013.01)

(58) Field of Classification Search
CPC ......................................... A61N 5/1007–1084
See application file for complete search history.

(56) References Cited

U.S. PATENT DOCUMENTS

| | | | | |
|---|---|---|---|---|
| 4,827,491 A | * | 5/1989 | Barish | A61N 5/1084 378/119 |
| 5,257,331 A | * | 10/1993 | Shapir | H01P 5/082 385/146 |
| 2006/0193435 A1 | * | 8/2006 | Hara | A61N 5/1049 378/65 |
| 2008/0129229 A1 | * | 6/2008 | Gatto | A61N 5/10 315/500 |
| 2010/0098214 A1 | * | 4/2010 | Star-Lack | A61B 6/04 378/65 |
| 2013/0231516 A1 | * | 9/2013 | Loo | A61N 5/1065 600/1 |
| 2014/0275708 A1 | * | 9/2014 | Leek | A61N 5/1077 600/1 |

OTHER PUBLICATIONS

Stanford University, School of Medicine, "Radiosurgery/Cyberknife", Sep. 3, 2007, 1 page.

(Continued)

*Primary Examiner* — Thaddeus B Cox
(74) *Attorney, Agent, or Firm* — Vista IP Law Group, LLP

(57) ABSTRACT

A medical device includes: a base; a positioner coupled to the base; an accelerator coupled to the positioner, wherein the positioner is operable to rotate the accelerator relative to the base about at least two axes; and a power source coupled to the accelerator, the power source configured to provide microwave power for the accelerator, wherein a position of the power source relative to the base remains fixed during movement of the accelerator. A medical device includes: a base; a positioner coupled to the base; an accelerator coupled to the positioner; a power source configured to provide microwave power for the accelerator, wherein a position of the source relative to the base remains fixed during movement of the accelerator; and a waveguide for coupling the power source and the accelerator; wherein the waveguide has a first segment with a first cross section, the first cross section being a circular cross-section.

30 Claims, 3 Drawing Sheets

(56) References Cited

OTHER PUBLICATIONS

Coste-Manière, E. et al. "Robotic Whole Body Stereotactic Radiosurgery: Clinical Advantages of the CyberKnife® Integrated System". Robotics Online, Mar. 1, 2005, 8 pages.

Accuray, "Accuray Announces Four New Products at Nation's Leading Radiation Oncology Meeting", accuray.com. Oct. 29, 2007, 2 pages.

Inoue, M.; Sato, K.; Koike, I. (2006). "2722". International Journal of Radiation Oncology*Biology*Physics. 66 (3): S611, 2 pages.

Accuray, "Xsight Spine Tracking System" Accuray, Feb. 10, 2009, 2 pages.

Accuray, "Xsight Lung Tracking System" Accuray, Feb. 10, 2009, 1 page.

Schweikard, A; Shiomi, H; Adler, J. "Respiration tracking in radiosurgery without fiducials". The International Journal of Medical Robotics and Computer Assisted Surgery. 1 (2): 19-27, Abstract, Jan. 2005, 1 page.

CyberKnife Radiosurgery—Fiducial Overview. sdcyberknife.com, Feb. 22, 2012, 2 pages.

Fuller CD; Scarbrough TJ (2006). "Fiducial Markers in Image-guided Radiotherapy of the Prostate". US Oncological Disease. 1 (2): 75-9, 5 pages.

Murphy, M. J.. "Fiducial-based targeting accuracy for external-beam radiotherapy". Medical Physics. 29 (3): 334-44, Feb. 20, 2002, 11 pages.

Schweikard, A; Glosser, G; Bodduluri, M; Murphy, M. J.; Adler, J. R. (2000). "Robotic motion compensation for respiratory movement during radiosurgery". Computer Aided Surgery. 5 (4): 263-77, Jan. 6, 2010, 16 pages.

Schweikard, A; Shiomi, H; Adler, J (2004). "Respiration tracking in radiosurgery". Medical physics. 31 (10): 2738-41, Jun. 1, 2004, 4 pages.

Muacevic, Alexander et al., "Single-Session Lung Radiosurgery Using Robotic Image-Guided Real-Time Respiratory Tumor Tracking". Cureus, Dec. 9, 2009, 4 pages.

Koong, A. C.; et al., "Phase I study of stereotactic radiosurgery in patients with locally advanced pancreatic cancer". International Journal of Radiation Oncology*Biology*Physics. vol. 58, No. 4, 1017-21, 2004, 5 pages.

Accuray, "RoboCouch Patient Positioning System" Accuray, Feb. 12, 2009, 2 pages.

Chang, S. D.; Main, W; Martin, D. P.; Gibbs, I. C.; Heilbrun, M. P. (2003). "An analysis of the accuracy of the Cyber Knife: A robotic frameless stereotactic radiosurgical system". Neurosurgery. 52 (1): 140-6; discussion 146-7, Abstract, 1 page.

Koong, A. C., et al., "Phase II study to assess the efficacy of conventionally fractionated radiotherapy followed by a stereotactic radiosurgery boost in patients with locally advanced pancreatic cancer". International Journal of Radiation Oncology*Biology*Physics. 63 (2): 320-3, 2005, 4 pages.

Lieskovsky, Y. C., et al., "Phase I Dose Escalation Study of Cyber Knife Stereotactic Radiosurgery for Liver Malignancies". International Journal of Radiation Oncology*Biology*Physics. 63, 2005, 1 page.

Hara, W.; Patel, D.; Pawlicki, T.; Cotrutz, C.; Presti, J.; King, C. (2006). "2206". International Journal of Radiation Oncology*Biology*Physics. 66 (3), 2 pages.

Gerszten, P. C.; Ozhasoglu, C; Burton, S. A.; Vogel, W. J.; Atkins, B. A.; Kalnicki, S; Welch, W. C. (2004). "Cyber Knife frameless stereotactic radiosurgery for spinal lesions: Clinical experience in 125 cases". Neurosurgery. 55 (1): 89-98; discussion 98-9.

Liao, J. J., et al., "Cyber Knife Fractionated Stereotactic Radiosurgery for the Treatment of Primary and Recurrent Head and Neck Cancer". International Journal of Radiation Oncology*Biology*Physics. 63: S381, Oct. 1, 2005, 3 pages.

Bhatnagar, A. K., et al., "Cyber Knife Frameless Radiosurgery for the treatment of extracranial benign tumors". Technology in cancer research & treatment. 4 (5): 571-6, Oct. 2005, 6 pages.

Thomas, Liz, DailyMail.com, "Patrick Swayze smiling again after 'miracle' response to cancer treatment". Mail Online, (Jul. 21, 2008), 35 pages.

Reuters, "Accuray Achieves Milestone of 150th CyberKnife System Installed Worldwide", Dec. 8, 2008, 2 pages.

pressreleasepoint.com , "Accuray Reaches 100th U.S. CyberKnife System Installation", Dec. 24, 2008, Accuray, 2 pages.

uwamedicalphysics.com, "CyberKnife in the Media", May 1, 2014, 1 page.

* cited by examiner

Section A-A

Section B-B

TREATMENT ENERGY DELIVERY SYSTEM

FIELD

The field of the application relates to medical devices, and more particularly, to medical devices that include accelerators.

BACKGROUND

Radiation therapy involves medical procedures that selectively deliver high doses of radiation to certain areas inside a human body. Also, particle (e.g., electron, proton, etc.) beam treatment may be used to provide certain treatments. In either radiation therapy or particle beam treatment, the medical device delivering the treatment energy has an accelerator and a power source for providing microwave power for the accelerator.

New medical device that includes an accelerator is described herein.

SUMMARY

A medical device includes: a base; a positioner coupled to the base; an accelerator coupled to the positioner, wherein the positioner is operable to rotate the accelerator relative to the base about at least two axes; and a power source coupled to the accelerator, the power source configured to provide microwave power for the accelerator, wherein a position of the power source relative to the base remains fixed during movement of the accelerator.

Optionally, the power source is coupled to the base.

Optionally, the power source is supported on a floor and is away from the base.

Optionally, the positioner comprises a robotic arm system.

Optionally, the robotic arm system comprises a first arm with a first end and a second end, and a second arm with a third end and a fourth end.

Optionally, the positioner comprises a ring gantry.

Optionally, the accelerator is configured to provide a particle beam, and wherein the medical device further comprise a target for interacting with the particle beam to generate treatment radiation.

Optionally, the treatment radiation has an energy level that is anywhere from 6 MeV to 10 MeV.

Optionally, the treatment radiation has a dose rate that is anywhere from 50 to 100 Gy/min.

Optionally, an isocenter associated with the treatment radiation is variable.

Optionally, the medical device further includes a collimator configured to collimate the radiation.

Optionally, the accelerator is configured to provide a particle beam as treatment energy.

Optionally, the particle beam has an energy level that is higher than 1 MeV, higher than 6 MeV, or higher than 75 MeV Optionally, the medical device further includes a waveguide for coupling the power source and the accelerator.

Optionally, at least a part of the waveguide has a circular cross-section.

Optionally, the waveguide comprises a first waveguide part and a second waveguide part that is moveably coupled to the first waveguide part.

Optionally, the second waveguide part is moveably coupled to the first waveguide part via a rotary joint.

Optionally, at least a segment of the waveguide is located within the positioner.

Optionally, the waveguide has a first segment with a first cross section, and a second segment with a second cross section that is different from the first cross section.

Optionally, the second cross section comprises a rectangular cross section, and the second segment interfaces with the accelerator.

Optionally, the positioner is free from at least a majority of a weight of the power source.

Optionally, the medical device further includes a radiation shielding carried by the positioner.

Optionally, the power source comprises a klystron.

A medical device includes: a base; a positioner coupled to the base; an accelerator coupled to the positioner; a power source coupled to the accelerator, the power source configured to provide microwave power for the accelerator, wherein a position of the source relative to the base remains fixed during movement of the accelerator; and a waveguide for coupling the power source and the accelerator; wherein the waveguide has a first segment with a first cross section, the first cross section being a circular cross-section.

Optionally, the waveguide comprises a first waveguide part and a second waveguide part that is moveably coupled to the first waveguide part, the first waveguide part comprising the first segment.

Optionally, the second waveguide part is moveably coupled to the first waveguide part via a rotary joint.

Optionally, at least the first segment of the waveguide is located within the positioner.

Optionally, the power source comprises a klystron.

Optionally, the positioner comprises a robotic arm system.

Optionally, the waveguide has a second segment with a second cross section that is different from the first cross section.

Optionally, the second cross section comprises a rectangular cross section, and the second segment interfaces with the accelerator.

Other and further aspects and features will be evident from reading the following detailed description.

DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only exemplary embodiments and are not therefore to be considered limiting in the scope of the claims.

DETAILED DESCRIPTION

Figure 1:
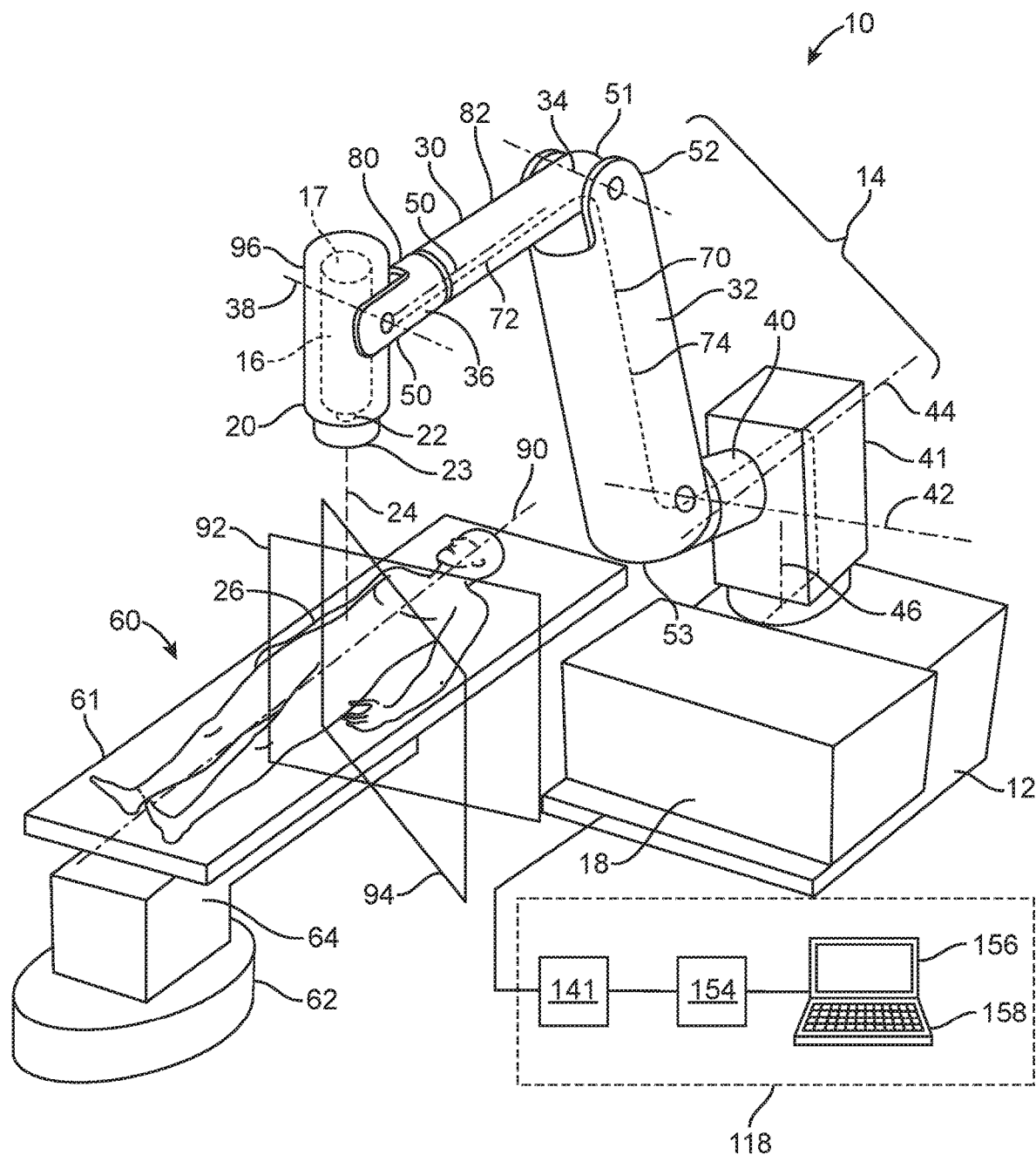
FIG. 1 illustrates a medical device in accordance with some embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

FIG. 1 illustrates a medical device 10 in accordance with some embodiments. The medical device 10 includes a base 12, a positioner 14 coupled to the base 12, and an accelerator 16 coupled to the positioner 14. The positioner 14 is operable to rotate the accelerator 16 relative to the base 12 about at least two axes. The medical device 10 also includes a particle source 17 for generating particles and accelerating particles (e.g., electrons, protons, etc.), and a power source 18 coupled to the accelerator 16. The power source 18 is configured to provide microwave power for the accelerator 16, which accelerates the particles from the particle source 17. In the illustrated embodiments, a position of the power source 18 relative to the base 12 remains fixed during movement of the accelerator 16 by the positioner 14.

In some embodiments, the power source 18 may be a klystron, such as a x-band klystron. Use of the klystron is advantageous over magnetron because magnetron restricts output dose-rate due to low peak and average power limits, especially at X-band. Also, use of the higher peak power available from a klystron may allow for a shorter accelerator structure. However, in other embodiments, the power source 18 may be a magnetron. In further embodiments, the power source 18 may be other types of device configured to provide microwave power for the accelerator 16. It should be noted that the power source 18 is not limited to having the size and shape shown in the illustrated example, and that the power source 18 may have other sizes and shapes. For example, in some cases, the power source 18 may have a bulky configuration, and may have a dimension that is 3 feet or more in height, a width that is 2 feet or more, and a length that is 4 feet or more. In some cases, the power source 18 may occupy a volume that is at least 20 cubic feet.

As shown in the figure, the power source 18 is coupled to the base 12. Alternatively, the power source 18 may be supported on a floor and is away from the base 12. Attaching the power source 18 to the base 12 or to the floor is advantageous. This is because such configuration allows the positioner 14 to be free from at least a majority of a weight of the power source 18. Also, if the power source 18 is mounted at the treatment head 96, the treatment head 96 will be more bulky, which may limit versatility in delivering certain treatments, and the medical device 10 may not perform as well in terms of serviceability and voltage hold-off. Furthermore, removing the weight of the power source 18 from the treatment head 96 allows a more robust radiation shielding to be placed at the treatment head 96, and also provides more room for the collimator 23 to provide better collimation. It may also provide a more sophisticated multi-leaf collimator (MLC) to be used due the increased weight limit. In some embodiments, the medical device 10 also includes a pulse transformer, which may also be supported by the base 12 or on the floor.

In some embodiments, the entire weight of the medical device 10 is 500 kg or less, or more preferably less than 400 kg, and even more preferably less than 300 kg. In other embodiments, the weight of the medical device 10 may be more than 500 kg.

In the illustrated embodiments, the positioner 14 includes, or is a part of, a robotic arm system. The robotic arm system includes a first arm 30 with a first end 50 and a second end 51, and a second arm 32 with a third end 52 and a fourth end 53. The accelerator 16 is rotatably coupled to the first end 50 of the first arm 30 so that the accelerator 16 is rotatable relative to the first end 50 about axis 38. The second end 51 of the first arm 30 is rotatably coupled to the first end 52 of the second arm 32, so that the first arm 30 is rotatable relative to the second arm 32 about axis 34. The robotic arm system also includes a member 40 to which the second end 53 of the second arm 32 is rotatably coupled, thereby allowing the second member 32 to rotate relative to the member 40 about axis 42. The member 40 is rotatably coupled to member 41 so that the member 40 is rotatable relative to the member 41 about axis 44. Also, the member 41 is rotatably coupled to the base 12 so that the member 41 is rotatable relative to the base 12 about axis 46. As shown in the figure, the first arm 30 has a first arm portion 80 with the first end 36, and a second arm portion 82 with the second end 34. The first arm portion 80 is rotatable relative to the second arm portion 82 about a longitudinal axis 50 of the first arm 30.

It should be noted that the robotic arm system is not limited to the configuration shown in the example, and that the robotic arm system may have other configurations in other embodiments. For example, in other embodiments, the second arm 32 may also have two arm portions that can be rotated relative to each other about a longitudinal axis of the second arm 32 (like the first arm 30). Also, in other embodiments, the first arm 30 may have a telescopic feature in which a first arm portion is translatable relative to a second arm portion along the longitudinal axis 50 of the first arm 30. Similarly, the second arm 32 may have a telescopic feature in which a first arm portion of the second arm 32 is translatable relative to a second arm portion along a longitudinal axis of the second arm 32. In further embodiments, the member 40 may be translatable relative to the member 41. For example, the member 40 may move along the axis 44. Furthermore, in other embodiments, the member 41 may be translatable relative to the base 12 (e.g., the member 41 may move up and down relative to the base 18).

The positioner 14 is advantageous because it provides various degrees of freedom for the accelerator 16. The positioner 14 is operable to translate the accelerator 16 along one axis (e.g., X, Y, or Z axis), along two axes (e.g., X and Y axes, X and Z axes, or Y and Z axes), or along three axes (e.g., X, Y, and Z axes). The positioner 14 is also operable to rotate the accelerator 16 about one axis (e.g., X, Y, or Z axis), about two axes (e.g., X and Y axes, X and Z axes, or Y and Z axes), or about three axes (e.g., X, Y, Z axes). In some cases, the positioner 14 may be configured to rotate the accelerator 16 around the patient 26 within a first plane, and also to rotate the accelerator 16 around the patient 26 within a second plane that is different from the first plane. It should be noted that the positioner 14 is not limited to providing all of the above degrees of freedom for the accelerator 16, and that the positioner 14 may provide only one or some of the degrees of freedom mentioned previously.

Figure 2:
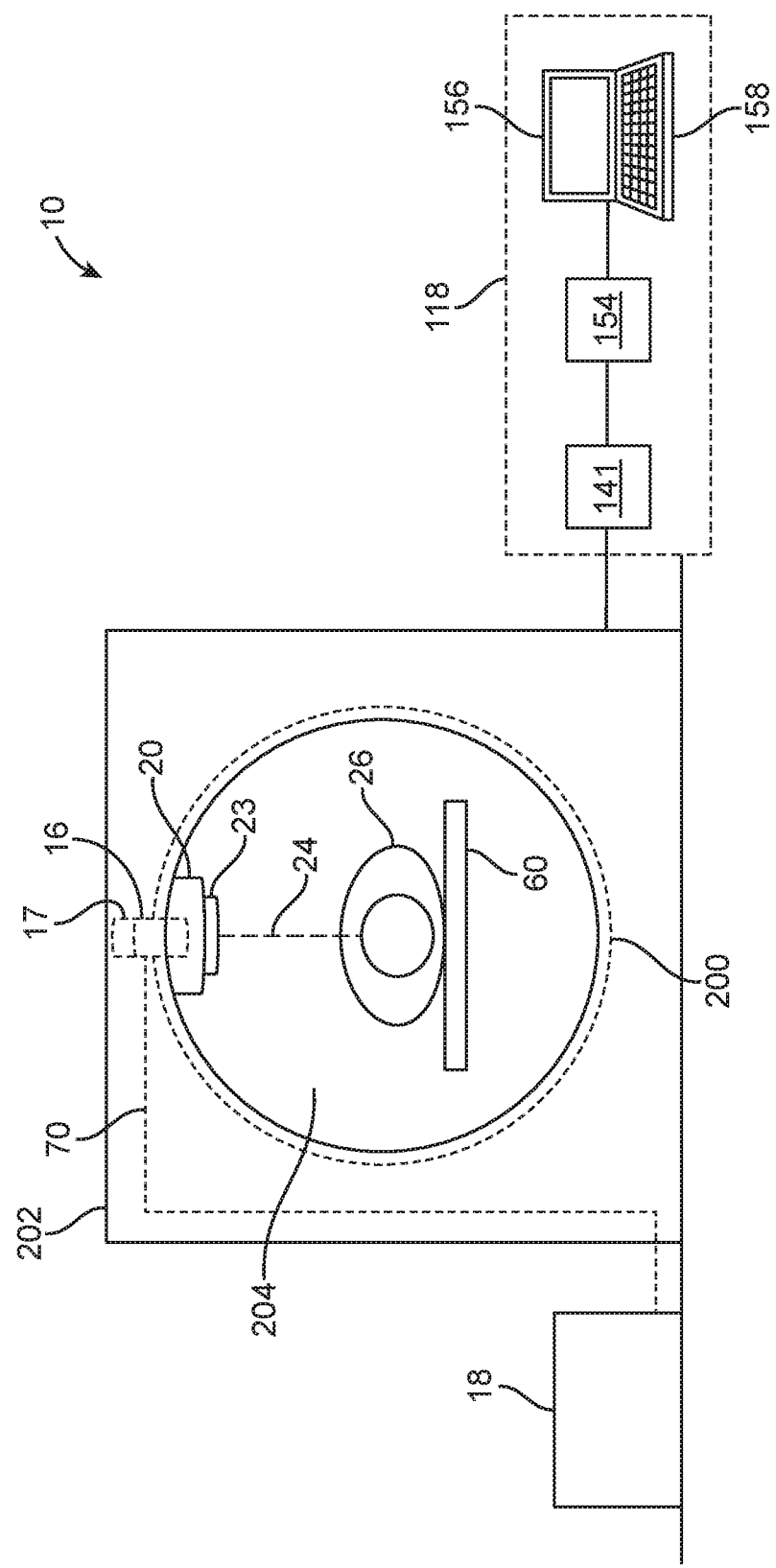
FIG. 2 illustrates another medical device in accordance with some embodiments.

In other embodiments, instead of a robotic arm system, the positioner 14 may include a ring gantry (FIG. 2). As shown in the figure, the ring gantry 200 may be implemented in a structure 202 having a bore 204. The accelerator 16 is coupled to the ring gantry 200, which rotates the accelerator 16. In some cases, the medical device 10 may include a double gimbal or ring with various degrees of freedom to implement non-coplanar treatments.

Returning to FIG. 1, the accelerator 16 is configured to provide a particle beam. The accelerator 16 has a plurality of cavities aligned along a longitudinal axis of the accelerator 16. The accelerator 16 is mounted at a head of the medical device 10 so that the last cavity (i.e., the output cavity) of the accelerator 16 outputs a particle beam towards a direction of the patient 26. The medical device 10 further includes a target 22 for interacting with the particle beam to generate treatment radiation. The medical device 10 also includes a collimator 23 configured to collimate the treatment radiation to form a radiation beam 24. In other embodiments, the medical device 10 may not include the target 22. In such cases, the accelerator 16 is configured to provide a particle beam (e.g., electron beam, proton beam, etc.) as treatment energy. In some cases, if proton beam is used directly for treatment, then the accelerator may be implemented using a dielectric wall accelerator that has a short configuration. As shown in the figure, the medical device 10 further includes a housing 20 for containing the accelerator 16. The accelerator 16, any component thereof, the collimator 23, or any component thereof, any particle beam output, or any treatment beam output may be considered to be an example of an energy source.

In some cases, the treatment radiation or the particle beam (e.g., electron beam, proton beam, etc.) may have an energy level that is anywhere from 6 MeV to 10 MeV. In other cases, the treatment radiation or the particle beam may have an energy level that is less than 6 MeV (e.g., 30 keV or greater), or that is more than 10 MeV. In some embodiments, if a particle beam (e.g., proton beam, electron beam, etc.) is used directly for treatment, then the particle beam may have an energy level that is higher than 30 keV, such as higher than 1 MeV, higher than 6 MeV, or higher than 75 MeV. In some cases, if electron beam is used directly for treatment, the electron beam may have an energy level that is anywhere from 6 MeV to 75 MeV. Also, in some cases, if proton beam is used directly for treatment, the proton beam may have an energy level that is anywhere from 50 MeV to 200 MeV, such as anywhere from 50 MeV to 80 MeV, or anywhere from 75 MeV to 200 MeV. Also, in some cases, the treatment radiation or the particle beam may have a dose rate that is anywhere from 50 to 100 Gy/min. In other cases, the treatment radiation or the particle beam may have a dose rate that is less than 50 Gy/min or more than 100 Gy/min. Also, in the illustrated embodiments, an isocenter associated with the treatment radiation is variable. Such feature may allow dose rates that can be more than an order of magnitude higher than what is currently available. For electrons and protons treatment, the difference may be in the order of 10 to 100 times.

In the illustrated embodiments, the medical device 10 further includes a waveguide 70 (illustrated schematically in dashed lines) for coupling the power source 18 and the accelerator 16. The waveguide 70 is configured to transmit microwave power provided by the power source 18 to the accelerator 16. As shown in the figure, the waveguide 70 comprises a first waveguide part 72 and a second waveguide part 74 that is moveably coupled to the first waveguide part 72. The waveguide 70 will be described in further detail with reference to FIG. 3.

In the illustrated embodiments, at least a segment of the waveguide 70 is located within the positioner 14. In other embodiments, a majority or an entirety of the waveguide 70 may be located outside the positioner 14. For example, the waveguide 70 may be secured to exterior parts of the positioner 14.

As shown in FIG. 1, the medical device 10 may be configured to work with, or may optionally further include, a patient support system 60. The patient support system 60 includes a patient support 61, and a positioner 64 configured to move the patient support 61. The positioner 64 may be supported on a base 62 that is either secured to a floor or configured to move relative to the floor. In some cases, the positioner 64 may be configured to translate the patient support 61 along one axis (e.g., X, Y, or Z axis), along two axes (e.g., X and Y axes, X and Z axes, or Y and Z axes), or along three axes (e.g., X, Y, and Z axes). The positioner 64 is also operable to rotate the patient support 61 about one axis (e.g., a vertical axis), about two axes (e.g., a vertical axis and a horizontal axis), or about three axes (e.g., X, Y, Z axes). In other embodiments, the patient support system 60 may not include the positioner 64, and the patient support 61 may be fixedly coupled to the base 62.

As shown in the figure, the medical device 10 also includes a control system 118. In the illustrated embodiments, the control system 118 includes a processing unit 154, such as a processor, coupled to a control 141. The control system 118 may also include a monitor 156 for displaying data and an input device 158, such as a keyboard or a mouse, for inputting data. The operation of the particle source 17, the accelerator 16, the positioner 14, and the collimator 22 may be controlled by the control 141, which provides power and timing signals to the particle source 17, the accelerator 16, the positioner 14, and the collimator 22. In some cases, the control system 118 may also control a movement of the patient support 60. For example, the control system 118 may provide control signals for operating the positioner 64 of the patient support 60. Although the control 141 is shown as a separate component from the processing unit 154, in alternative embodiments, the control 141 can be a part of the processing unit 154. In some embodiments, the control system 118 may also include a treatment planning system.

During use of the medical device 10, the patient 26 is supported on the patient support 61, and the patient 26 is placed at an operative position with respect to the medical device 10. The processing unit 154 executes a treatment plan stored in a non-transitory medium, which causes the control 141 to operate one or more components of the medical device 10. For example, the treatment plan may prescribes that an energy source of the radiation beam (or energy beam) 24 be positioned at a certain distance from the patient 26, and be moved at least partially around the patient 26 through a certain range gantry angles while treatment energy is being delivered to the patient 26. The treatment plan may also prescribe different cross sectional shapes of the beam 24 be created by the collimator 23 at certain respective gantry angles. For example, the energy source may be moved around the patient 26 within a plane 92 that is perpendicular to a longitudinal axis 90 of the patient 26. Alternatively, or additionally, the energy source may be moved around the patient 26 within another plane 94 that forms a non-perpendicular angle with respect to the longitudinal axis 90 of the patient 26. In some cases, the treatment plan may prescribe that the energy source be moved around the patient 26 in more than two rotational planes. Also, if the patient support system 60 includes the positioner 64, the treatment plan may also prescribe that the patient support 61 be positioned (e.g., rotated about a vertical axis) to thereby allow the energy source be rotated around the patient within different rotational planes.

In some cases, how well the medical device 10 can deliver treatment energy from different angles towards a target may be quantified using the metric, solid angle. If the medical device 10 is capable of delivering treatment beam from all three-dimensional angles around a point at a target, then the center line of the beam from all of the angles will traverse all surface area of a sphere around the point (with the sphere being a distance r from the point). The surface area of a sphere is $4\pi r^2$. Accordingly, if the medical device 10 can deliver treatment beam from all three-dimensional angles around a point at a target, the corresponding solid angle will have an area of $4\pi r^2$. On the other hand, if the medical device 10 can deliver treatment beam from only a subset of all three-dimensional angles around a point at a target, the corresponding solid angle will be less than $4\pi r^2$.

In some embodiments, the movement of the energy source and/or a delivery of the beam 24 may be synchronized with a physiological cycle (e.g., a breathing and/or a cardiac movement) of the patient 26. Because the treatment head 96 of the medical device 10 is free from the weight of the power source 18, the treatment head 96 may be moved and/or stopped very quickly (compared to the configuration in which the power source 18 is supported by the positioner 14). For example, a motion of a patient's chest may be associated with motion of a lung tumor, and the treatment head 96 and/or the leaves of the collimator may be moved in correspondence with a movement of the patient's chest. In one implementation, the medical device 10 may include a patient position monitor, which monitors the movement of the patient 26. For example, the patient position monitor may include a camera that views one or more fiducials (e.g., markers, patient landmarks, etc.) associated with the patient 26. The images from the camera may be processed by a processing unit, which determines phases of a physiological cycle (e.g., breathing cycle) based on the processed images. The determined phases may be used by the processing unit 154 of the control system 118 to operate the medical device 10. For example, the processing unit 154 may generate one or more control signals to move the positioner 14 in correspondence (e.g., in synchronization) with the determined phases, and/or to operate the accelerator 16 and/or the collimator 23 in correspondence with the determined phase. The processing unit 154 may also generate one or more control signals to gate a delivery of the beam 24 based on the determined phases. In other embodiments, instead of using a camera, an imaging device (e.g., MRI, x-ray, CT, etc.) may be used to generate images of internal structures of the patient. The images may include implant markers, and may be processed by the processing unit 154 to determine phases of the patient's physiological cycle. Alternatively, images of internal tissue of the patient may be used as fiducial for allowing the processing unit 154 to determine phases of the patient's physiological cycle.

In other embodiments, the patient 26 may be instructed to perform breath-hold while the medical device 10 delivers the beam 24 from different gantry angles. Because the movement of the head 96 may be carried out efficiently, the duration of the patient's breath-hold will be relatively shorter (compared to the configuration in which the weight of the power source 18 is supported by the positioner 24).

Figure 3:
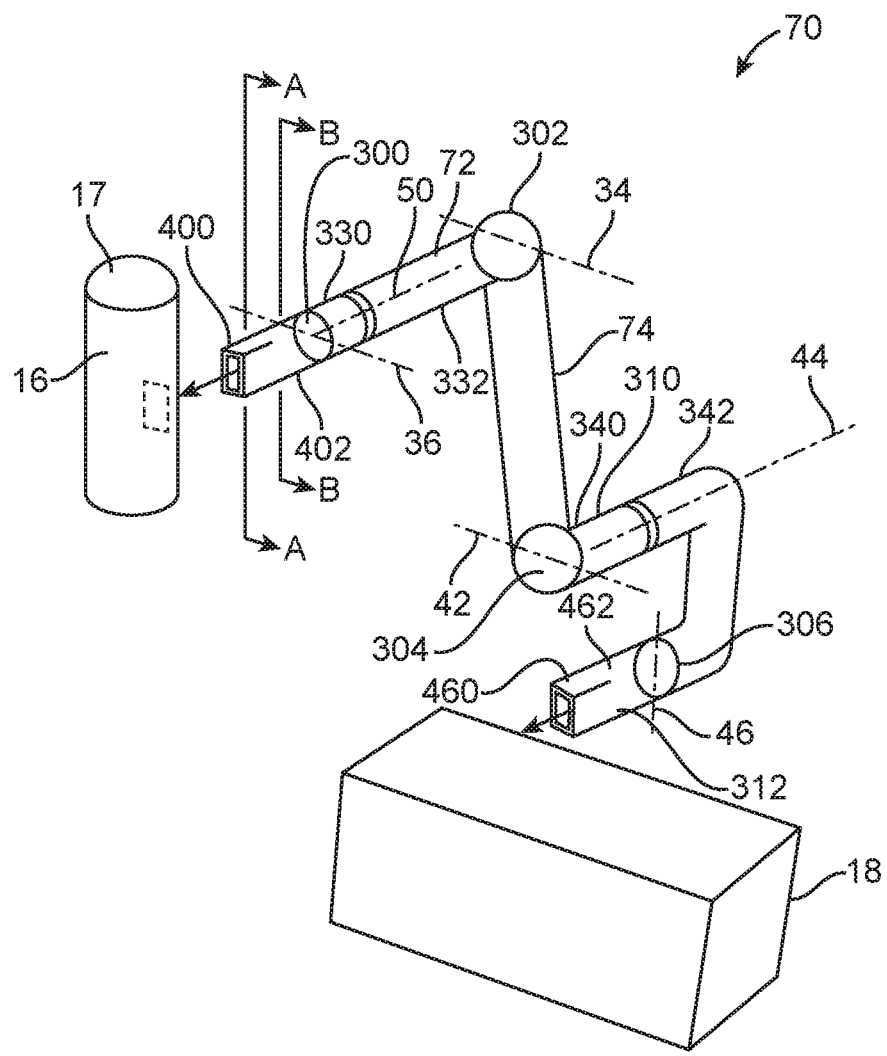
FIG. 3 illustrates a waveguide.

FIG. 3 illustrates the waveguide 70 in further detail. The waveguide 70 is configured to transmit microwave energy from the power source 18 (e.g., klystron) to the accelerator 16. The waveguide 70 includes multiple portions that correspond with the respective components of the positioner 14, so that the waveguide 70 has degrees of movement that correspond with those associated with the positioner 14. This allows the portions of the waveguide 70 to move in correspondence with the respective components of the positioner 14.

In particular, the waveguide 70 includes a first rotary joint 300 that corresponds with the axis 36, which allows the waveguide 70 to accommodate the rotational movement of the accelerator 16 around the axis 36 with respect to the first arm 30 of the positioner 14.

The waveguide 70 also includes a second rotary joint 302 that corresponds with the axis 34, which allows the first waveguide part 72 to rotate relative to the second waveguide part 74, thereby accommodating the rotational movement of the first arm 30 with respect to the second arm 32 around the axis 34.

The waveguide 70 also includes a third rotary joint 304 that corresponds with the axis 42, which allows the second waveguide part 74 to rotate relative to a third waveguide part 310, thereby accommodating the rotational movement of the second arm 32 with respect to the member 40 around the axis 42.

The waveguide 70 also includes a fourth rotary joint 306 that corresponds with the axis 46, which allows the third waveguide part 310 to rotate about the axis 46 with respect to a fourth waveguide part 312, thereby accommodating the rotational movement of the member 40 and member 41 about the axis 46 with respect to the base 12.

Also, the first waveguide part 72 may optionally have a telescopic feature, in which a first portion 330 of the first waveguide part 72 is translatable relative to a second portion 332 of the first waveguide part 72 along a longitudinal axis of the first waveguide part 72 (or the longitudinal axis 50 of the first arm 30).

The third waveguide part 310 may also optionally have a telescopic feature, in which a first portion 340 of the third waveguide part 310 is translatable relative to a second portion 342 of the third waveguide part 310 along a longitudinal axis of the third waveguide part 310 (or the longitudinal axis 44).

Figure 4:
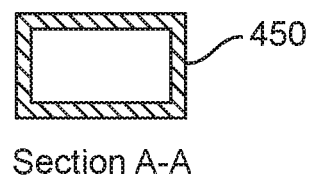
FIG. 4 illustrates two cross sections of the waveguide of FIG. 3.
Figure 4:
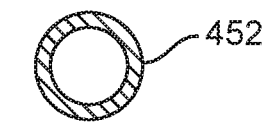

As shown in the figure, the first waveguide part 72 has a first segment 400 that interfaces with the accelerator 16, and a second segment 402 that is further away from the accelerator 16. The first segment 400 may have a cross sectional shape that is different from that of the second segment 402. For example, the first segment 400 may have a non-circular cross section 450 (e.g., a rectangular cross section, elliptical cross section, etc.), while the second segment 402 has a circular cross section 452 (FIG. 4). In some cases, a majority of the length of the waveguide 70 has a circular cross section, which is relatively less lossy (compared to rectangular cross section). In such cases, the circular cross section transitions to a rectangular cross section (achieving a mode conversion) at the location where the waveguide 70 interfaces with the accelerator 16. In other embodiments, the first segment 400 interfacing the accelerator 16 may also include a circular cross section. In further embodiments, the second segment 402 may have a non-circular cross section, such as an elliptical cross section (which may keep field rotation minimized or aligned), a rectangular cross section, etc. Also, in other embodiments, at least a majority of the length of the waveguide 70 may have a rectangular cross section.

Similarly, the fourth waveguide part 312 may have a first segment 460 that interfaces with the power source 18, and a second segment 462 that is further away from the power source 18. The first segment 460 of the fourth waveguide part 312 may have a non-circular cross section (e.g., an elliptical cross section, a rectangular cross section, etc.), while the second segment 462 may have a circular cross section. In other embodiments, the first segment 460 of the fourth waveguide part 312 interfacing the power source 18 may also include a circular cross section. In further embodiments, the second segment 462 of the fourth waveguide part 312 may have a non-circular cross section, such as an elliptical cross section, a rectangular cross section, etc.

The waveguide 70 is advantageous because it provides various degrees of freedom for the accelerator 16. The waveguide 70 is moveable in correspondence with the positioner 14 while the positioner 14 translates the accelerator 16 along one axis (e.g., X, Y, or Z axis), along two axes (e.g., X and Y axes, X and Z axes, or Y and Z axes), or along three axes (e.g., X, Y, and Z axes). The waveguide 70 is also moveable in correspondence with the positioner 14 while the positioner 14 rotates the accelerator 16 about one axis (e.g., X, Y, or Z axis), about two axes (e.g., X and Y axes, X and Z axes, or Y and Z axes), or about three axes (e.g., X, Y, Z axes). In some cases, the waveguide 70 may be configured to allow the accelerator 16 to rotate around the patient 26 within a first plane, and also to allow the accelerator 16 to rotate around the patient 26 within a second plane that is different from the first plane. It should be noted that the waveguide 70 is not limited to providing all of the above degrees of freedom for the accelerator 16, and that the waveguide 70 may provide only one or some of the degrees of freedom mentioned previously.

In one implementation, the waveguide 70 may be configured to operate at a frequency band that is anywhere from 2.6 to 3.95 GHz. In other embodiments, the waveguide 70 may be configured to operate at a frequency that is lower than 2.6 GHz, or higher than 3.95 GHz. Also, in some embodiments, the waveguide 70 may have a cutoff frequency of lowest order mode that is 2.078 GHz, and a cutoff frequency of upper mode that is 4.156 GHz. In other embodiments, the waveguide 70 may have a cutoff frequency of lowest order mode that is lower than 2.078 GHz or higher than 2.078 GHz. Also, in other embodiments, the waveguide 70 may have a cutoff frequency of upper mode that is lower than 4.156 GHz or higher than 4.156 GHz.

Also, in some embodiments, the waveguide 70 may have a rectangular cross section that is 2.84 inches by 1.34 inches in dimension. In other embodiments, the waveguide 70 may have a rectangular cross section with dimensions that are different from those described. Furthermore, in some embodiments, the waveguide 70 may be a S-band waveguide, a C-band waveguide, or a X-band waveguide.

In any of the embodiments described herein, the medical device 10 may further include a radiation shielding carried (e.g., supported) by the positioner 14 and/or by the base 12. The radiation shield is configured to achieve non-occupational exposure levels of 2 mR/hr or less in nearby uncontrolled areas of a facility (such as, within 10 meters from the system 10, and more preferably within 5 meters from the medical device 10, and more preferably within 3 meters from the medical device 10, and even more preferably within a distance of 1.5 m from the system 10—e.g., measured from an isocenter or from any surface of the system 10). Additionally, or alternatively, the shielding of the medical device 10 may be configured to achieve occupational exposure levels of 5 mR/hr or less are preferably achieved at the control console in the treatment room (such as, within 10 meters from the medical device 10, and more preferably within 5 meters from the medical device 10, and more preferably within 3 meters from the medical device 10, and even more preferably within a distance of 1.5 m from the medical device 10—e.g., measured from an isocenter or from any surface of the system 10). Additionally, or alternatively, in one or more embodiments, the shielding of the medical device 10 may be configured to satisfy the requirements under 10 CFR § 20.1301, which prescribes dose limits for individual members of the public. For example, in some embodiments, the shielding for the medical device 10 may be configured so that (1) the total effective dose equivalent to individual members of the public does not exceed 0.1 rem (1 mSv) in a year, and (2) the dose in any unrestricted area from external sources does not exceed 0.002 rem (0.02 millisievert) in any one hour.

Although particular embodiments have been shown and described, it will be understood that it is not intended to limit the claimed inventions to the preferred embodiments, and it will be obvious to those skilled in the art that various changes and modifications may be made without department from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A medical device comprising:
a base;
a positioner coupled to the base;
an accelerator coupled to the positioner, wherein the positioner is operable to rotate the accelerator relative to the base about at least two axes;
a waveguide; and
a power source coupled to the accelerator via the waveguide, the power source configured to provide microwave power for the accelerator, wherein a position of the power source relative to the base remains fixed during movement of the accelerator;
wherein the waveguide has an arm with opposite ends, wherein the arm comprises a first rectilinear tubular segment and a second rectilinear tubular segment, wherein at least a part of the first rectilinear tubular segment and at least a part of the second rectilinear tubular segment are located between the opposite ends of the arm, the first rectilinear tubular segment having a first lumen with a first cross section, the second rectilinear tubular segment having a second lumen with a second cross section that is different from the first cross section of the first lumen, wherein the first lumen with the first cross section extends along a longitudinal axis of the arm, and wherein the second lumen with the second cross section extends along the longitudinal axis of the arm.

2. The medical device of claim 1, wherein the power source is coupled to the base.

3. The medical device of claim 1, wherein the power source is supported on a floor and is away from the base.

4. The medical device of claim 1, wherein the positioner comprises a robotic arm system.

5. The medical device of claim 4, wherein the robotic arm system comprises a first arm with a first end and a second end, and a second arm with a third end and a fourth end.

6. The medical device of claim 1, wherein the positioner comprises a ring gantry.

7. The medical device of claim 1, wherein the accelerator is configured to provide a particle beam, and wherein the medical device further comprises a target for interacting with the particle beam to generate treatment radiation.

8. The medical device of claim 7, wherein the treatment radiation has an energy level that is anywhere from 6 MeV to 10 MeV.

9. The medical device of claim 7, wherein the treatment radiation has a dose rate that is anywhere from 50 to 100 Gy/min.

10. The medical device of claim 7, wherein an isocenter associated with the treatment radiation is variable.

11. The medical device of claim 7, further comprising a collimator configured to collimate the radiation.

12. The medical device of claim 1, wherein the accelerator is configured to provide a particle beam as treatment energy.

13. The medical device of claim 12, wherein the particle beam has an energy level that is higher than 1 MeV.

14. The medical device of claim 1, wherein at least a part of the waveguide has a circular cross-section.

15. The medical device of claim 1, wherein the waveguide comprises a first waveguide part and a second waveguide part that is moveably coupled to the first waveguide part.

16. The medical device of claim 15, wherein the second waveguide part is moveably coupled to the first waveguide part via a rotary joint.

17. The medical device of claim 1, wherein at least a portion of the waveguide is located within the positioner.

18. The medical device of claim 1, wherein the second cross section comprises a rectangular cross section, and the second rectilinear tubular segment interfaces with the accelerator.

19. The medical device of claim 1, wherein the positioner is free from at least a majority of a weight of the power source.

20. The medical device of claim 1, further comprising a radiation shielding carried by the positioner.

21. The medical device of claim 1, wherein the power source comprises a klystron.

22. The medical device of claim 1, wherein the second cross section of the second rectilinear tubular segment that is different from the first cross section is interfacing with the accelerator.

23. A medical device comprising:
a base;
a positioner coupled to the base;
an accelerator coupled to the positioner;
a power source coupled to the accelerator, the power source configured to provide microwave power for the accelerator, wherein a position of the source relative to the base remains fixed during movement of the accelerator; and
a waveguide for coupling the power source and the accelerator;
wherein the waveguide has an arm with opposite ends, wherein the arm comprises a first rectilinear tubular segment and a second rectilinear tubular segment, wherein at least a part of the first rectilinear tubular segment and at least a part of the second rectilinear tubular segment are located between the opposite ends of the arm, the first rectilinear tubular segment having a first lumen with a first cross section, the first cross section being a circular cross-section, the second rectilinear tubular segment having a second lumen with a second cross section that is different from the first cross section of the first lumen, wherein the first lumen with the first cross section extends along a longitudinal axis of the arm, and wherein the second lumen with the second cross section extends along the longitudinal axis of the arm.

24. The medical device of claim 23, wherein the waveguide comprises a first waveguide part and a second waveguide part that is moveably coupled to the first waveguide part, the first waveguide part comprising the first rectilinear tubular segment.

25. The medical device of claim 24, wherein the second waveguide part is moveably coupled to the first waveguide part via a rotary joint.

26. The medical device of claim 23, wherein at least the first rectilinear tubular segment of the waveguide is located within the positioner.

27. The medical device of claim 23, wherein the power source comprises a klystron.

28. The medical device of claim 23, wherein the positioner comprises a robotic arm system.

29. The medical device of claim 23, wherein the second cross section comprises a rectangular cross section, and the second rectilinear tubular segment interfaces with the accelerator.

30. The medical device of claim 23, wherein the second cross section of the second rectilinear tubular segment that is different from the first cross section is interfacing with the accelerator.

* * * * *